United States Patent
Halbrecht

(10) Patent No.: US 10,918,415 B2
(45) Date of Patent: Feb. 16, 2021

(54) METHOD AND SYSTEM FOR PATELLA TENDON REALIGNMENT

(71) Applicant: ZKR ORTHOPEDICS, INC., San Francisco, CA (US)

(72) Inventor: Jeffrey Halbrecht, San Francisco, CA (US)

(73) Assignee: ZKR ORTHOPEDICS, INC., San Francisco, CA (US)

( * ) Notice: Subject to any disclaimer, the term of this patent is extended or adjusted under 35 U.S.C. 154(b) by 35 days.

(21) Appl. No.: 16/380,635

(22) Filed: Apr. 10, 2019

(65) Prior Publication Data

US 2019/0231391 A1 Aug. 1, 2019

Related U.S. Application Data

(60) Division of application No. 15/728,209, filed on Oct. 9, 2017, now abandoned, which is a continuation of
(Continued)

(51) Int. Cl.
*A61F 2/08* (2006.01)
*A61B 17/58* (2006.01)
(Continued)

(52) U.S. Cl.
CPC .............. *A61B 17/58* (2013.01); *A61F 2/08* (2013.01); *A61F 2/38* (2013.01); *A61F 2/389* (2013.01);
(Continued)

(58) Field of Classification Search
CPC .............. A61B 2/08; A61B 2002/2835; A61B 2002/3839; A61B 2/28; A61B 2/2846;
(Continued)

(56) References Cited

U.S. PATENT DOCUMENTS 3,872,519 A 3/1975 Giannestras et al.
3,879,767 A 4/1975 Stubstad
(Continued)

FOREIGN PATENT DOCUMENTS

EP 2298179 A2 3/2011

OTHER PUBLICATIONS

Chow et al.; Fracture of the tibial tubercle in the adolescent; The Journal of Bone and Joint Surgery; 72(2); pp. 231-234; Mar. 1, 1990.
(Continued)

*Primary Examiner* — Alvin J Stewart
(74) *Attorney, Agent, or Firm* — Shay Glenn LLP

(57) ABSTRACT

A method and system provide and use a patellar implant. The patellar implant includes a superior portion, an inferior portion opposite to the superior portion, and an anterior portion. The superior portion being configured to reside below a patellar tendon and to elevate and/or tilt the patellar tendon. The inferior portion is configured to be seated in proximity to a tibia. The anterior portion is between the superior portion and the inferior portion. The anterior portion is placed in proximity to a patella. In one aspect, the method includes inserting the implant beneath the patellar tendon and between the patella and a position at which the patellar tendon is affixed to the tibia. In this aspect, the method also includes affixing the implant.

18 Claims, 9 Drawing Sheets

Related U.S. Application Data application No. 13/653,936, filed on Oct. 17, 2012, now Pat. No. 9,808,287, which is a division of application No. 12/671,478, filed as application No. PCT/US2008/071629 on Jul. 30, 2008, now abandoned.

(60) Provisional application No. 60/953,325, filed on Aug. 1, 2007.

(51) Int. Cl.
*A61F 2/38* (2006.01)
*A61F 2/28* (2006.01)

(52) U.S. Cl.
CPC .......... *A61F 2002/2892* (2013.01); *A61F 2220/0016* (2013.01); *A61F 2220/0033* (2013.01); *A61F 2230/001* (2013.01); *A61F 2230/0034* (2013.01); *A61F 2230/0093* (2013.01); *A61F 2230/0095* (2013.01); *A61F 2250/0009* (2013.01); *A61F 2250/0026* (2013.01); *A61F 2250/0036* (2013.01); *A61F 2250/0037* (2013.01); *A61F 2250/0051* (2013.01); *A61F 2250/0063* (2013.01); *A61F 2310/00017* (2013.01); *A61F 2310/00023* (2013.01); *A61F 2310/00029* (2013.01); *A61F 2310/00395* (2013.01); *A61F 2310/00976* (2013.01)

(58) Field of Classification Search
CPC .......... A61B 2002/285; A61B 17/8061; A61B 17/8095; A61B 17/56; A61B 17/562; A61B 17/58; A61F 2/4202; A61F 2/4455; A61F 2/4465; A61F 2/38; A61F 2/3836; A61F 2/3872; A61F 2/3877
See application file for complete search history.

(56) References Cited

U.S. PATENT DOCUMENTS

| | | |
|---|---|---|
| 3,886,599 A | 6/1975 | Schlein |
| 3,889,300 A | 6/1975 | Smith |
| 3,964,106 A | 6/1976 | Hutter et al. |
| 4,007,495 A | 2/1977 | Frazier |
| 4,041,550 A | 8/1977 | Frazier |
| 4,052,753 A | 10/1977 | Dedo |
| 4,069,518 A * | 1/1978 | Groth, Jr. ............... A61F 2/4202 623/21.18 |
| 4,156,944 A | 6/1979 | Schreiber et al. |
| 4,158,894 A | 6/1979 | Worrell |
| 4,164,793 A | 8/1979 | Swanson |
| 4,285,070 A | 8/1981 | Averill |
| 4,470,158 A | 9/1984 | Pappas et al. |
| 4,642,122 A | 2/1987 | Steffee |
| 4,650,490 A | 3/1987 | Figgie |
| 4,759,766 A | 7/1988 | Buettner Janz et al. |
| 4,904,261 A | 2/1990 | Dove et al. |
| 4,955,915 A * | 9/1990 | Swanson ............... A61F 2/4261 623/21.14 |
| 5,019,104 A | 5/1991 | Whiteside et al. |
| 5,035,700 A | 7/1991 | Kenna |
| 5,152,790 A | 10/1992 | Rosenberg et al. |
| 5,197,986 A | 3/1993 | Mikhail |
| 5,231,977 A | 8/1993 | Graston |
| 5,258,032 A | 11/1993 | Bertin |
| 5,314,481 A | 5/1994 | Bianco |
| 5,326,364 A * | 7/1994 | Clift, Jr. ............... A61F 2/4241 606/286 |
| 5,383,937 A | 1/1995 | Mikhail |
| 5,425,775 A | 6/1995 | Kovacevic et al. |
| 5,480,443 A | 1/1996 | Elias |
| 5,544,993 A | 8/1996 | Harle |
| 5,545,229 A | 8/1996 | Parsons et al. |
| 5,571,139 A | 11/1996 | Jenkins |
| 5,571,198 A | 11/1996 | Drucker et al. |
| 5,580,353 A | 12/1996 | Mendes et al. |
| 5,643,272 A | 7/1997 | Haines et al. |
| 5,676,667 A | 10/1997 | Hausman |
| 5,702,460 A | 12/1997 | Carls et al. |
| 5,702,465 A | 12/1997 | Burkinshaw |
| 5,702,467 A | 12/1997 | Gabriel et al. |
| 5,733,287 A | 3/1998 | Tepic et al. |
| 5,824,106 A | 10/1998 | Fournol |
| 5,879,386 A | 3/1999 | Jore |
| 5,888,203 A | 3/1999 | Goldberg |
| 6,132,468 A | 10/2000 | Mansmann |
| 6,143,032 A | 11/2000 | Schafer et al. |
| 6,146,423 A | 11/2000 | Cohen et al. |
| 6,200,347 B1 | 3/2001 | Anderson et al. |
| 6,245,110 B1 | 6/2001 | Grundei et al. |
| 6,280,474 B1 | 8/2001 | Cassidy et al. |
| 6,302,915 B1 | 10/2001 | Cooney et al. |
| 6,315,798 B1 | 11/2001 | Ashby et al. |
| 6,368,326 B1 | 4/2002 | Dakin et al. |
| 6,371,985 B1 | 4/2002 | Goldberg |
| 6,409,767 B1 | 6/2002 | Pericé et al. |
| 6,468,314 B2 | 10/2002 | Schwartz et al. |
| 6,520,964 B2 | 2/2003 | Tallarida et al. |
| 6,527,794 B1 | 3/2003 | McDevitt et al. |
| 6,579,318 B2 | 6/2003 | Varga et al. |
| 6,589,248 B1 | 7/2003 | Hughes |
| 6,592,622 B1 | 7/2003 | Ferguson |
| 6,599,321 B2 | 7/2003 | Hyde |
| 6,616,696 B1 | 9/2003 | Merchant |
| 6,626,945 B2 | 9/2003 | Simon et al. |
| 6,632,247 B2 | 10/2003 | Boyer et al. |
| 6,679,914 B1 | 1/2004 | Gabbay |
| 6,702,821 B2 | 3/2004 | Bonutti |
| 6,709,460 B2 | 3/2004 | Merchant |
| 6,712,856 B1 * | 3/2004 | Carignan ............... A61B 34/10 623/20.35 |
| 6,719,794 B2 | 4/2004 | Gerber et al. |
| 6,800,094 B2 | 10/2004 | Burkinshaw |
| 6,814,757 B2 | 11/2004 | Kopylov et al. |
| 6,824,567 B2 | 11/2004 | Tornier et al. |
| 6,852,330 B2 | 2/2005 | Bowman et al. |
| 6,854,330 B2 | 2/2005 | Potter |
| 6,855,150 B1 | 2/2005 | Linehan |
| 6,866,684 B2 | 3/2005 | Fell et al. |
| 6,890,358 B2 | 5/2005 | Ball et al. |
| 6,893,463 B2 | 5/2005 | Fell et al. |
| 6,896,702 B2 | 5/2005 | Collazo |
| 6,905,513 B1 | 6/2005 | Metzger |
| 6,911,044 B2 | 6/2005 | Fell et al. |
| 6,916,341 B2 | 7/2005 | Rolston |
| 6,926,739 B1 | 8/2005 | O'Connor et al. |
| 6,966,928 B2 | 11/2005 | Fell et al. |
| 6,974,480 B2 | 12/2005 | Messerli et al. |
| 6,994,730 B2 | 2/2006 | Posner |
| 7,004,971 B2 | 2/2006 | Serhan et al. |
| 7,008,452 B2 | 3/2006 | Hawkins |
| 7,011,687 B2 | 3/2006 | Deffenbaugh et al. |
| 7,025,790 B2 * | 4/2006 | Parks ............... A61B 17/15 623/21.11 |
| 7,060,073 B2 | 6/2006 | Frey et al. |
| 7,105,025 B2 | 9/2006 | Castro et al. |
| 7,105,027 B2 | 9/2006 | Lipman et al. |
| 7,124,762 B2 | 10/2006 | Carter et al. |
| 7,160,333 B2 | 1/2007 | Plouhar et al. |
| 7,163,563 B2 | 1/2007 | Schwartz et al. |
| 7,182,787 B2 | 2/2007 | Hassler et al. |
| 7,226,482 B2 | 6/2007 | Messerli et al. |
| 7,291,169 B2 | 11/2007 | Hodorek |
| 7,297,161 B2 | 11/2007 | Fell |
| 7,323,012 B1 | 1/2008 | Stone et al. |
| 7,341,602 B2 | 3/2008 | Fell et al. |
| 7,476,225 B2 | 1/2009 | Cole |
| 7,479,160 B2 | 1/2009 | Branch et al. |
| 7,485,147 B2 | 2/2009 | Pappas et al. |
| 7,500,991 B2 | 3/2009 | Bartish et al. |
| 7,534,270 B2 | 5/2009 | Ball |

(56) References Cited

U.S. PATENT DOCUMENTS

| | | | |
|---|---|---|---|
| 7,544,210 B2 | 6/2009 | Schaefer et al. | |
| 7,572,291 B2 | 8/2009 | Gil et al. | |
| 7,618,454 B2 * | 11/2009 | Bentley | A61F 2/4455 |
| | | | 623/17.11 |
| 7,632,311 B2 | 12/2009 | Seedhom et al. | |
| 7,637,953 B2 | 12/2009 | Branch et al. | |
| 7,641,689 B2 | 1/2010 | Fell et al. | |
| 7,722,676 B2 | 5/2010 | Hanson et al. | |
| 7,723,395 B2 | 5/2010 | Ringeisen et al. | |
| 7,726,319 B1 | 6/2010 | Boyce | |
| 7,749,276 B2 | 7/2010 | Fitz | |
| 7,758,651 B2 | 7/2010 | Chauhan et al. | |
| 7,780,670 B2 | 8/2010 | Bonutti | |
| 7,806,898 B2 | 10/2010 | Justin et al. | |
| 7,815,645 B2 | 10/2010 | Haines | |
| 7,819,918 B2 | 10/2010 | Malaviya et al. | |
| 7,875,082 B2 | 1/2011 | Naidu | |
| 7,879,105 B2 | 2/2011 | Schmieding et al. | |
| 7,896,921 B2 | 3/2011 | Smith et al. | |
| 7,896,923 B2 | 3/2011 | Blackwell et al. | |
| 7,959,675 B2 | 6/2011 | Gately | |
| 7,967,863 B2 | 6/2011 | Frey et al. | |
| 7,972,383 B2 * | 7/2011 | Goldstein | A61F 2/3877 |
| | | | 623/20.18 |
| 7,993,402 B2 | 8/2011 | Sidler | |
| 8,002,833 B2 | 8/2011 | Fabris Monterumici et al. | |
| 8,002,837 B2 | 8/2011 | Stream et al. | |
| 8,002,841 B2 | 8/2011 | Hasselman | |
| 8,034,117 B2 | 10/2011 | Matsuzaki et al. | |
| 8,043,375 B2 | 10/2011 | Strzepa et al. | |
| 8,043,380 B1 | 10/2011 | Park et al. | |
| 8,052,753 B2 | 11/2011 | Melvin | |
| 8,052,755 B2 | 11/2011 | Naidu | |
| 8,083,746 B2 | 12/2011 | Novak | |
| 8,088,168 B2 | 1/2012 | Hassler et al. | |
| 8,092,544 B2 * | 1/2012 | Wright | A61F 2/3877 |
| | | | 623/20.18 |
| 8,114,156 B2 | 2/2012 | Hatch | |
| 8,128,704 B2 | 3/2012 | Brown et al. | |
| 8,142,503 B2 | 3/2012 | Malone | |
| 8,257,444 B2 | 9/2012 | Linares | |
| 8,372,078 B2 | 2/2013 | Collazo | |
| 9,808,287 B2 | 11/2017 | Halbrecht | |
| 2001/0023371 A1 | 9/2001 | Bonutti | |
| 2002/0029084 A1 | 3/2002 | Paul et al. | |
| 2002/0091447 A1 | 7/2002 | Shimp et al. | |
| 2002/0107574 A1 | 8/2002 | Boehm et al. | |
| 2002/0133230 A1 * | 9/2002 | Repicci | A61F 2/3868 |
| | | | 623/14.12 |
| 2003/0083751 A1 * | 5/2003 | Tornier | A61F 2/3877 |
| | | | 623/20.18 |
| 2003/0088315 A1 | 5/2003 | Supinski | |
| 2003/0100950 A1 | 5/2003 | Moret | |
| 2003/0109928 A1 | 6/2003 | Pasquet et al. | |
| 2003/0120344 A1 | 6/2003 | Michelson | |
| 2003/0120346 A1 | 6/2003 | Mercinek et al. | |
| 2003/0125807 A1 | 7/2003 | Lambrecht et al. | |
| 2003/0138329 A1 | 7/2003 | Koyano et al. | |
| 2003/0171757 A1 | 9/2003 | Coon et al. | |
| 2003/0204265 A1 | 10/2003 | Short et al. | |
| 2004/0039395 A1 | 2/2004 | Coon et al. | |
| 2004/0117020 A1 | 6/2004 | Frey et al. | |
| 2004/0127990 A1 * | 7/2004 | Bartish, Jr. | A61F 2/4611 |
| | | | 623/17.11 |
| 2004/0133278 A1 | 7/2004 | Marino et al. | |
| 2004/0143336 A1 | 7/2004 | Burkinshaw | |
| 2004/0143338 A1 * | 7/2004 | Burkinshaw | A61F 2/3877 |
| | | | 623/20.18 |
| 2004/0186585 A1 | 9/2004 | Feiwell | |
| 2004/0215195 A1 | 10/2004 | Shipp et al. | |
| 2004/0230303 A1 | 11/2004 | Gomes et al. | |
| 2004/0230315 A1 | 11/2004 | Ek | |
| 2004/0236428 A1 | 11/2004 | Burkinshaw et al. | |
| 2004/0243240 A1 | 12/2004 | Beaurain et al. | |
| 2005/0004671 A1 | 1/2005 | Ross et al. | |
| 2005/0027360 A1 | 2/2005 | Webb et al. | |
| 2005/0033424 A1 | 2/2005 | Fell | |
| 2005/0033426 A1 | 2/2005 | Ogilvie et al. | |
| 2005/0137708 A1 | 6/2005 | Clark | |
| 2005/0143822 A1 * | 6/2005 | Paul | A61F 2/4455 |
| | | | 623/17.16 |
| 2005/0222685 A1 | 10/2005 | Hayden et al. | |
| 2005/0267584 A1 | 12/2005 | Burdulis et al. | |
| 2005/0288788 A1 * | 12/2005 | Dougherty-Shah | |
| | | | A61F 2/4465 |
| | | | 623/17.11 |
| 2006/0036321 A1 * | 2/2006 | Henninger | A61F 2/4455 |
| | | | 623/17.11 |
| 2006/0074423 A1 | 4/2006 | Alleyne et al. | |
| 2006/0074492 A1 | 4/2006 | Frey | |
| 2006/0100715 A1 | 5/2006 | De Villiers | |
| 2006/0129243 A1 * | 6/2006 | Wong | A61F 2/4465 |
| | | | 623/17.16 |
| 2006/0142858 A1 | 6/2006 | Colleran et al. | |
| 2006/0161260 A1 | 7/2006 | Thomas et al. | |
| 2006/0276907 A1 | 12/2006 | Boyer et al. | |
| 2007/0027547 A1 * | 2/2007 | Rydell | A61F 2/4225 |
| | | | 623/21.18 |
| 2007/0129804 A1 * | 6/2007 | Bentley | A61F 2/4455 |
| | | | 623/17.11 |
| 2007/0129809 A1 | 6/2007 | Meridew et al. | |
| 2007/0173946 A1 | 7/2007 | Bonutti | |
| 2007/0203581 A1 | 8/2007 | Vanaclocha | |
| 2007/0208343 A1 * | 9/2007 | Magerl | A61B 17/025 |
| | | | 606/86 A |
| 2007/0233141 A1 | 10/2007 | Park et al. | |
| 2007/0265708 A1 | 11/2007 | Brown et al. | |
| 2007/0293947 A1 | 12/2007 | Mansmann | |
| 2007/0299528 A9 | 12/2007 | Lotke | |
| 2008/0021566 A1 | 1/2008 | Peters et al. | |
| 2008/0091270 A1 | 4/2008 | Miller et al. | |
| 2008/0097617 A1 | 4/2008 | Fellinger et al. | |
| 2008/0140094 A1 | 6/2008 | Schwartz et al. | |
| 2008/0154267 A1 | 6/2008 | Merchant et al. | |
| 2008/0154311 A1 | 6/2008 | Staeubli | |
| 2008/0154371 A1 | 6/2008 | Fell et al. | |
| 2008/0161815 A1 | 7/2008 | Schoenefeld et al. | |
| 2008/0161933 A1 | 7/2008 | Grotz et al. | |
| 2008/0172054 A1 | 7/2008 | Claypool et al. | |
| 2008/0195099 A1 | 8/2008 | Minas | |
| 2008/0234762 A1 | 9/2008 | Forstein et al. | |
| 2008/0262618 A1 | 10/2008 | Hermsen et al. | |
| 2008/0281422 A1 | 11/2008 | Schmieding | |
| 2008/0281425 A1 | 11/2008 | Thalgott et al. | |
| 2009/0012615 A1 | 1/2009 | Fell | |
| 2009/0088763 A1 | 4/2009 | Aram et al. | |
| 2009/0088846 A1 | 4/2009 | Myung et al. | |
| 2009/0118830 A1 | 5/2009 | Fell | |
| 2009/0130167 A1 | 5/2009 | Shelton et al. | |
| 2009/0164014 A1 | 6/2009 | Liljensten et al. | |
| 2009/0182433 A1 | 7/2009 | Reiley et al. | |
| 2009/0198341 A1 | 8/2009 | Choi et al. | |
| 2009/0210063 A1 * | 8/2009 | Barrett | A61F 2/44 |
| | | | 623/17.16 |
| 2009/0226068 A1 | 9/2009 | Fitz et al. | |
| 2009/0259311 A1 | 10/2009 | Shterling et al. | |
| 2009/0259312 A1 | 10/2009 | Shterling et al. | |
| 2009/0306783 A1 | 12/2009 | Blum | |
| 2009/0312807 A1 | 12/2009 | Boudreault et al. | |
| 2010/0023126 A1 | 1/2010 | Grotz | |
| 2010/0049322 A1 | 2/2010 | McKay | |
| 2010/0049325 A1 | 2/2010 | Biedermann et al. | |
| 2010/0057216 A1 * | 3/2010 | Gannoe | A61F 2/4684 |
| | | | 623/21.18 |
| 2010/0121355 A1 | 5/2010 | Gittings et al. | |
| 2010/0125266 A1 | 5/2010 | Deem et al. | |
| 2010/0131069 A1 | 5/2010 | Halbrecht | |
| 2010/0161057 A1 | 6/2010 | Berry et al. | |
| 2010/0198354 A1 * | 8/2010 | Halbrecht | A61F 2/38 |
| | | | 623/20.19 |
| 2010/0204798 A1 | 8/2010 | Gerbec et al. | |
| 2010/0262246 A1 | 10/2010 | Attia | |

(56) References Cited

U.S. PATENT DOCUMENTS

| | | |
|---|---|---|
| 2010/0292731 A1 | 11/2010 | Gittings et al. |
| 2010/0292733 A1 | 11/2010 | Hendricksen et al. |
| 2010/0305698 A1 | 12/2010 | Metzger et al. |
| 2011/0004305 A1 | 1/2011 | Jansson et al. |
| 2011/0054627 A1 | 3/2011 | Bear |
| 2011/0093073 A1 | 4/2011 | Gatt et al. |
| 2011/0172768 A1 | 7/2011 | Cragg et al. |
| 2011/0202138 A1 | 8/2011 | Shenoy et al. |
| 2011/0213466 A1 | 9/2011 | Shenoy et al. |
| 2011/0238180 A1 | 9/2011 | Fritz et al. |
| 2011/0270393 A1 | 11/2011 | Marvel |
| 2011/0288643 A1 | 11/2011 | Linder-Ganz et al. |
| 2012/0022649 A1 | 1/2012 | Robinson et al. |
| 2012/0065640 A1 | 3/2012 | Metzger et al. |
| 2013/0060343 A1 | 3/2013 | Halbrecht |
| 2013/0131802 A1 | 5/2013 | Halbrecht |
| 2018/0028229 A1 | 2/2018 | Halbrecht |

OTHER PUBLICATIONS

Gaasbeek et al.; The influence of open and closed high tibial osteotomy on dynamic patellar tracking: a biomechanical study; Knee surg. Sports Traumatol. Arthrosc.; 15(8); pp. 978-984; Aug. 1, 2007.

Maquet; Biomechanical treatment of patellofemoral osteoarthritis. Advancement of the patellar tendon: review of rheumatism and osteoarticular diseases, National Library of Medicine; vol. 30; issue 12; pp. 780-785; 1963.

Zimmer; Nex Gen trabecular metal augmentation patella, Surgical technique; 4 pages; retrieved from the internet (http://www.zimmer.com/content/dam/zimmer-web/documents/en-US/pdf/surgical-techniques/knee/NexGen-Trabecular-Metal-Augmentation-Patella-Surgical-Technique-97-7255-004-00-Rev-24-2008.pdf) on Dec. 29, 2017.

Halbrecht; U.S. Appl. No. 16/380,649 entitled "Method and system for patella tendon realignment," filed Apr. 10, 2019.

* cited by examiner

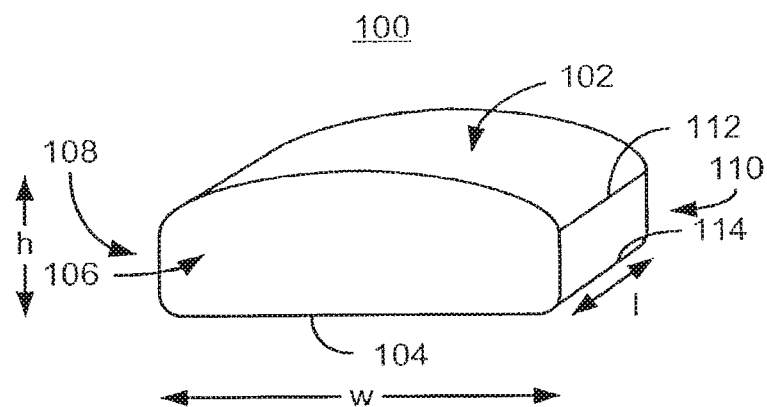
FIG. 1
FIG. 8
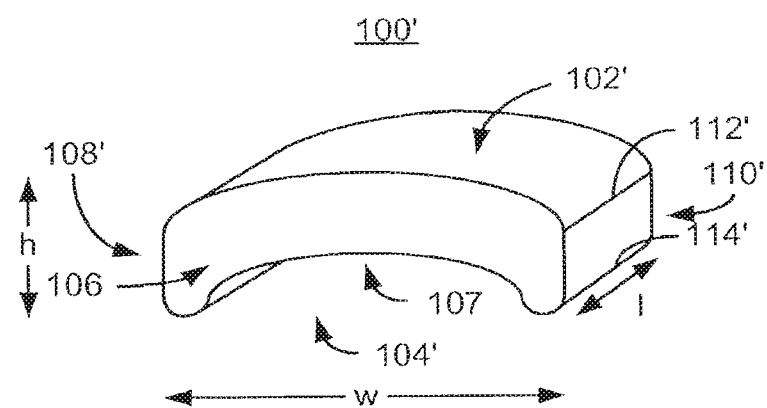
FIG. 2

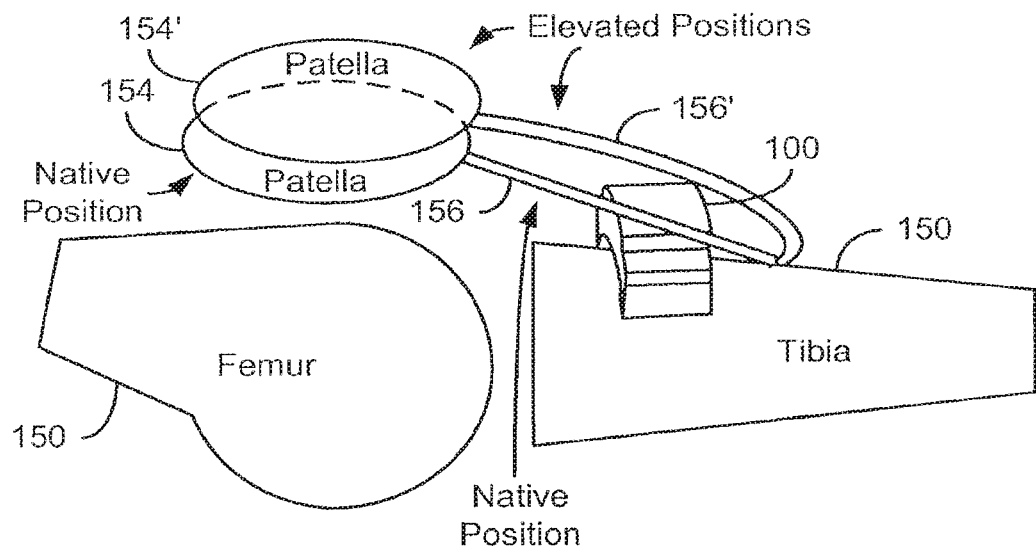
FIG. 7
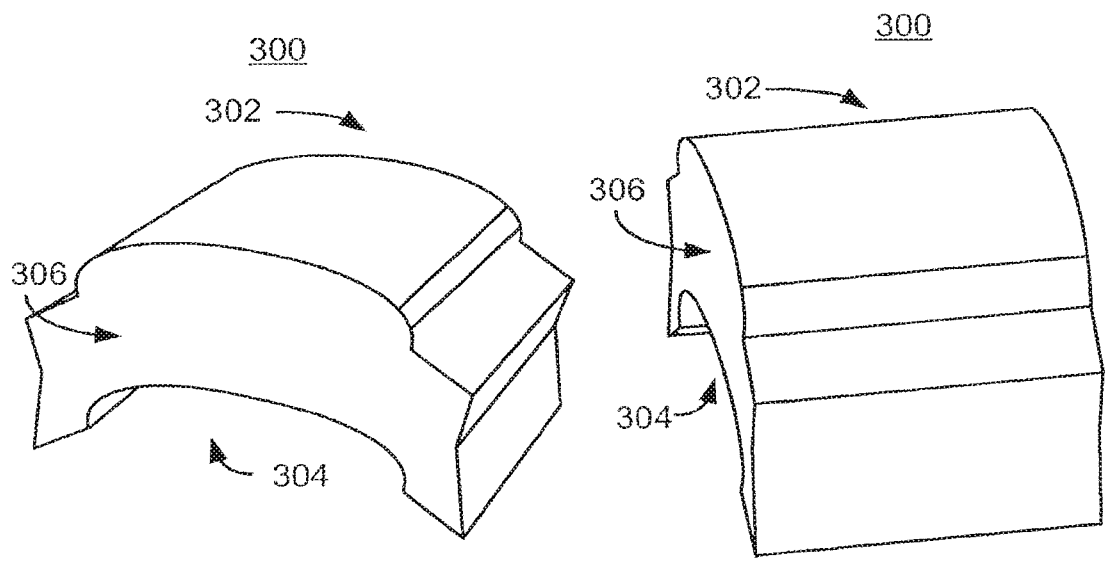
FIG. 8
FIG. 9

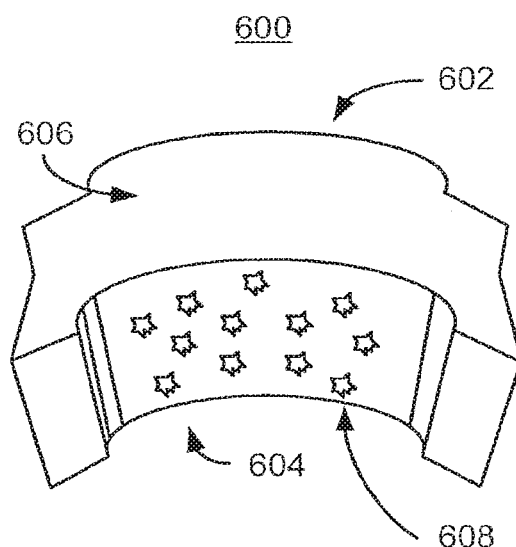
FIG. 13
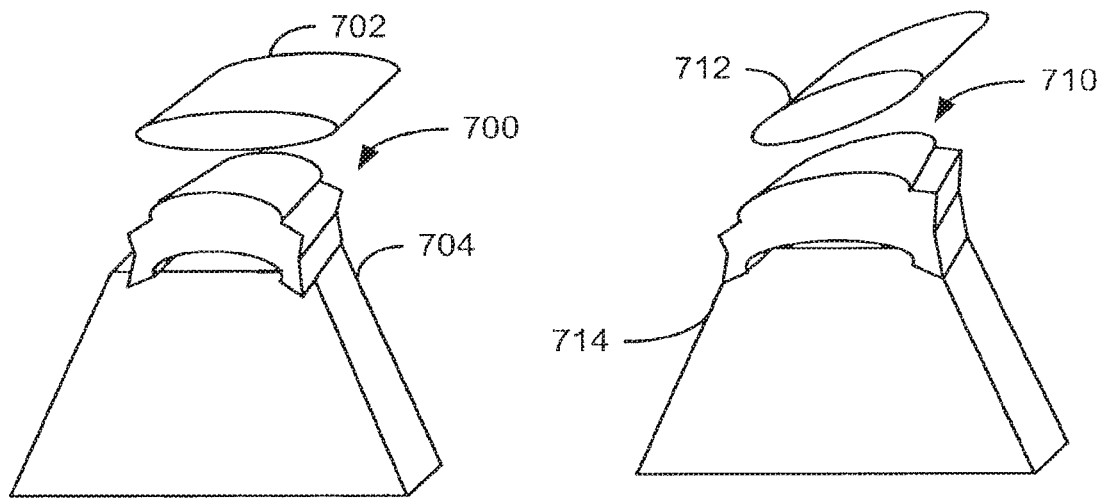
FIG. 14
FIG. 15

750

750

750

METHOD AND SYSTEM FOR PATELLA TENDON REALIGNMENT

CROSS REFERENCE TO RELATED APPLICATIONS

This application is a divisional of U.S. patent application Ser. No. 15/728,209, filed Oct. 9, 2017; which is a continuation of U.S. patent application Ser. No. 13/653,936, filed Oct. 17, 2012, now U.S. Pat. No. 9,808,287; which is a divisional of U.S. patent application Ser. No. 12/671,478, filed Jan. 29, 2010, now abandoned; which is a national stage application of International Application No. PCT/US08/071629, filed Jul. 30, 2008; which claims priority to U.S. Provisional Patent Application No. 60/953,325, filed Aug. 1, 2007, each of which is hereby incorporated herein by reference in its entirety.

BACKGROUND OF THE INVENTION

Problems of the patella-femoral joint are a common cause of knee pain. The pain may arise from issues such as poor alignment of the patella or from cartilage breakdown (chondromalacia or arthritis) behind the patella or on the opposing articular surface of the femoral groove (trochlea). Conventional surgical options for treating patella-femoral pain caused by malalignment, chondromalacia or arthritis may include realignment of the patella. For example tracking of the patella may be changed by tilting the patella or by moving the patella to one side or the other. Moving the patella forward (i.e., anteriorly) through a surgical procedure provides another conventional option for treating these conditions. This conventional technique is thought to decrease force across the patella-femoral joint and thus diminish the pain arising from excess force against a worn-out patellar or trochlear cartilage.

Although available, surgical options to realign the patella may be very invasive. For example, surgeries may involve cutting and fixating the bony attachment of the patellar tendon. In particular, conventional techniques may include detaching the patellar tendon from the tibia, then reattaching the patellar tendon at a new location to obtain the desired alignment of the patella. Such invasive surgical techniques may also result in prolonged recovery times. Consequently, an improved mechanism for treating patella-femoral joint problems such as patella-femoral pain, chondromalacia, and/or arthritis is desired.

BRIEF SUMMARY OF THE INVENTION

A patellar implant and a method for using the patellar implant are described. The patellar implant includes a superior portion, an inferior portion opposite to the superior portion, and an anterior portion. The superior portion being configured to reside below a patellar tendon and to elevate and/or tilt the patellar tendon. The inferior portion is configured to be seated in proximity to a tibia. The anterior portion is between the superior portion and the inferior portion. The anterior portion is placed in proximity to a patella. In one aspect, the method includes inserting the implant beneath the patellar tendon and between the patella and a position at which the patellar tendon is affixed to the tibia. In this aspect, the method also includes affixing the implant.

According to the method and system disclosed herein, the patellar implant may be used to realign, for example by elevating and/or tilting, the patellar tendon. As a result, various the patella-femoral joint problems may be alleviated.

BRIEF DESCRIPTION OF SEVERAL VIEWS OF THE DRAWINGS

FIG. 1 depicts an exemplary embodiment of a patellar implant.

FIG. 2 depicts another exemplary embodiment of a patellar implant.

FIG. 7 depicts an exemplary embodiment of one option for placement of an exemplary embodiment of a patellar implant to reposition the patellar tendon and patella.

FIGS. 8 and 9 depict another exemplary embodiment of a patellar implant.

FIG. 13 depicts another exemplary embodiment of a patellar implant.

FIGS. 14, 15, 16 and 17 depict other exemplary embodiments of patellar implants positioned beneath a patellar tendon.

DETAILED DESCRIPTION OF THE INVENTION

Figure 3:
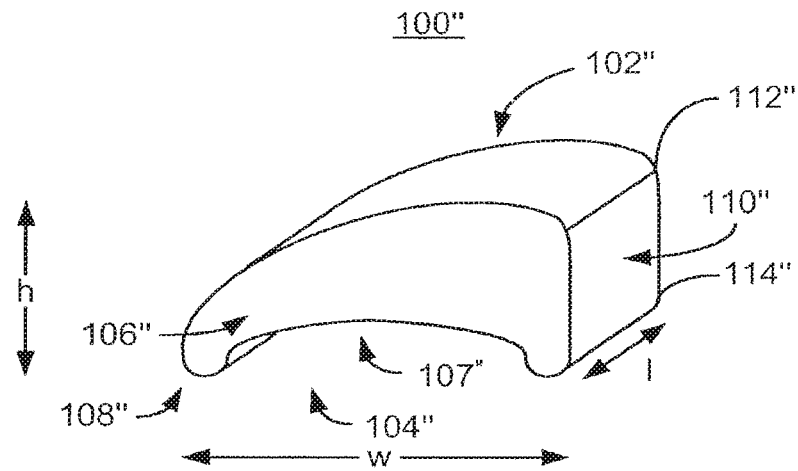
FIG. 3 depicts another exemplary embodiment of a patellar implant.

The method and system relate to medical devices, particularly implants. The following description is presented to enable one of ordinary skill in the art to make and use the invention and is provided in the context of a patent application and its requirements. Various modifications to the embodiments and the generic principles and features described herein will be readily apparent to those skilled in the art. Thus, the method and system are not intended to be limited to the embodiments shown, but is to be accorded the widest scope consistent with the principles and features described herein.

The method and system are mainly described in terms of particular systems provided in particular implementations. However, one of ordinary skill in the art will readily recognize that this method and system will operate effectively in other implementations. For example, the particular shape of the patellar implant may take a number of different forms depending upon, for example, the specific anatomy of a patient and the problem desired to be addressed. The method and system will also be described in the context of particular methods having certain steps. However, the method and system operate effectively for other methods having different and/or additional steps not inconsistent with the method and system.

FIG. 1 depicts an exemplary embodiment of a patellar implant 100. For clarity, FIG. 1 is not drawn to scale. The patellar implant includes a superior portion 102, an inferior portion 104, and an anterior portion 106. The patellar implant 100 includes a posterior portion (not shown) that is opposite to the anterior portion 106. In the embodiment shown, the posterior portion is substantially the same as and parallel to the anterior portion 106. Also shown are lateral surfaces 108 and 110 as well as edges 112 and 114.

The superior portion 102 is shown having a convex upper surface. In addition, the superior portion is symmetric. The superior portion 102 is to reside in proximity to the patellar tendon, while the inferior portion 104 is to reside in proximity to the tibia. The inferior portion 104 of the patellar implant 100 is substantially flat. The superior portion 102 is thus configured to lift and/or tilt the patellar tendon, while the surface of the inferior portion 104 is configured to fit the tibia. The amount of lift and/or tilt provided may depend upon the shape of the implant 100 as well as the positioning of the implant 100 in the patient. Consequently, the size and/or shape of the implant 100 may vary. For example, in some embodiments, the height, h, of the patellar implant 100 may be between 0.5 and 3 centimeters. In other embodiments, the height may vary between 1 and 2 centimeters. In some embodiments, the width, w, of the patellar implant 100 may be between 1 and 3.5 centimeters. In other embodiments, the width of the patellar implant 100 may vary between 2 and 3 centimeters. Similarly, in some embodiments, the length, L of the patellar implant may vary between one and 3.5 centimeters. In other embodiments, the length may vary between 1 and three centimeters. In other embodiments, other heights, widths, lengths, and/or angles between components may differ.

In use, the patellar implant 100 may be inserted through an incision in proximity to the patella. The patellar implant 100 is placed below the patellar tendon (not shown in FIG. 1) between the patella (not shown in FIG. 1) and a distal attachment of the patella (not shown in FIG. 1). In other words, the entire patellar implant 100 is placed between the patellar tendon and the tibia and between the patella and a location at which the patellar tendon attaches to the tibia. The location of the patellar implant 100, as well as its particular configuration, is selected to achieve the desired tilt and/or elevation of the patellar tendon and thus the desired repositioning of the patella. In the embodiment shown, the inferior portion 104 is flat. As a result, a slot or flat region may be formed in the tibia at the desired position of the patellar implant 100. The patellar implant 100 is then fitted on the slot such that the inferior portion 104 meets the flat region of the tibia. Once the patellar implant 100 is in the desired position, the patellar implant may be fixed in place, through a variety of mechanisms, described below. In some embodiments, the patellar implant 100 may then be affixed to the tibia, the patellar tendon, or both.

The patellar implant 100 may include various materials. Particular embodiments may include natural materials, synthetic materials, or a combination thereof. For example, the patellar implant 100 or portions thereof may be constructed using plastics, metals, synthetic bone materials, allografts and/or other materials. Examples of representative materials may include, but are not limited to, stainless steel, titanium, cobalt chrome, polyethylene, polyetheretherketone, and other materials. In some embodiments, the patellar implant 100 may be formed as a composite. For example the superior portion 102 may be made of different materials than the inferior portion 104. In another embodiment, the superior portion 102 and inferior portion 104 may be made of the same material(s). However, in either embodiment, the portions 102 and 104 may be formed as separate pieces, then joined together.

The use of different materials may allow the patellar implant 100 to adapt to the differential forces facing these surfaces. For example, composite patellar implant 100 may include a superior portion 102 fabricated from a polymeric material, with a metal inferior portion 104. This allows the polymeric material of the superior portion 102 to be in contact with the patellar tendon, while a textured surface on the metal of the inferior portion 104 contacts bone. Other arrangements and combinations might also be used. Coatings, adhesives, surfaces, and/or other features may be used, for example on the surface of the superior portion 102 and/or the surface of the inferior portion 104. Such treatments may be provided to facilitate local affixation, growth of the tendon and/or bone to the patellar implant 100, healing, and/or other desired outcomes. As an example, a bone ingrowth surface using metal beads, a bone morphogenic protein, or the like may be provided.

Although depicted with particular shape(s), the implant 100 and/or its components may take any shape that is anatomically acceptable for positioning beneath the patellar tendon and/or patella. For example, some edges of the patellar implant 100, such as the edge 112, is shown as being sharp. Other edges, such as the edge 114 are shown as being rounded. However, the particular shape of an edge may be altered. In another embodiment, the edge 112 might be rounded and/or the edge 114 sharp. Rounding of edges 112 and 114 may reduce stresses placed on the implant 100 during physiological use. Similarly, the surfaces of the implant 100 may be modified to conform to the anatomic position where the implant 100 is to be used. Thus, portions 102, 104, 106, 108, and 110 may have different shapes, placements, and/or angles with respect to each other. For example, although the superior portion 102 is shown having a symmetric, convex upper surface, the superior portion 102 may have a different shape. Other such shapes may include ridges that may be configured to position or adhere the patellar implant 100 to the portion(s) of the patient's anatomy. In other embodiments, ridges may be omitted. Similarly, the inferior portion 104 of the patellar implant is depicted as substantially flat. However, in another embodiment, the inferior portion 104 may have a different shape. Further, although lateral surfaces 108 and 110 are shown, in another embodiment, the surface 108 and/or 110 may be omitted, may not be planar, and/or may have a different shape.

Because the superior portion 102 elevates and/or tilts the patellar tendon, the patella may be repositioned. For example, the patella may be elevated and/or tilted. Without being bound by theory, it is understood that the elevation and/or tilting of the patella may alter patellar tracking and decrease forces on the patella, thereby treating patients with patella pain, chondromalacia of the patella or patellar malalignment. Consequently, pain and/or other issues related to patellar-femoral joint problems may be alleviated. For example, some patellar-femoral joint problems are due to the patella contacting the tibia or femur. Elevating or tilting the patella a desired amount using the implant 100 may provide space between the patella and the tibia or femur. The elevation of the patella may also decrease force loads across the patellar-femoral joint. As a result patellar pain, malalignment, chondromalacia, arthritis, and/or other issues involving the patellar-femoral joint may be treated.

FIG. 2 depicts another exemplary embodiment of a patellar implant 100'. For clarity, FIG. 2 is not drawn to scale. The components of the patellar implant 100' are analogous to the patellar implant 100 and are, therefore, labeled similarly. Thus, the patellar implant 100' includes a superior portion 102', an inferior portion 104', anterior portion 106', and posterior portion (not shown in FIG. 2). Also shown are lateral surfaces 108' and 110' as well as edges 112' and 114'. As for the patellar implant 100, the amount of lift and/or tilt of the patellar tendon may vary between patients. Consequently, the size, angles between, degree of rounding, and/or specific shape of the patellar implant 100' and portions 102', 104', 106', 107, 108', 110', 112', and 114' may also vary. Further, although lateral surfaces 108' and 110' are shown, in another embodiment, the surface 108' and/or 110' may be omitted. For example, the concave superior portion 102' may simple terminate at an edge 112' that is adjacent to the inferior portion 104'. In addition, the patellar implant 100' is used in a similar manner to and may be made from similar material(s) as the patellar implant 100.

The superior portion 102' is shown having a convex upper surface and being symmetric. The superior portion 102' is still configured to lift and/or tilt the patellar tendon. The superior portion 102' is still to reside in proximity to the patellar tendon, while the inferior portion 104' is configured to be placed in proximity to the tibia. The inferior portion 104' of the patellar implant 100' has a convex portion 107. In particular, the convex portion 107 is configured to fit the tibia of the patient. As a result, cutting, grinding, or other altering of the tibia in order to fit the implant 100' may be avoided. Once in place, the patellar implant 100' may be affixed in place through a variety of mechanisms, described below. The patellar implant 100' might be affixed to the tibia, the patellar tendon, or both.

Because the superior portion 102' is configured to elevate and/or tilt the patellar tendon, the patella may be repositioned. For example, the patella may be elevated and/or tilted. Consequently, pain and/or other issues related to patellar-femoral joint problems may be alleviated. In addition, because cutting or other alteration of the tibia may be avoided, recovery time and ease of use of the patellar implant 100' may be improved.

FIG. 3 depicts another exemplary embodiment of a patellar implant 100". For clarity, FIG. 3 is not drawn to scale. The components of the patellar implant 100" are analogous to the patellar implants 100 and 100'. Thus, the components of the patellar implant 100" are labeled similarly. The patellar implant 100" includes a superior portion 102", an inferior portion 104", anterior portion 106", and posterior portion (not shown in FIG. 3). However, the patellar implant 100" is wedge shaped. In particular, lateral surface 108/108' has been replaced with a rounded edge 108". As for the patellar implants 100 and 100', the amount of lift and/or tilt of the patellar tendon may vary between patients. Consequently, the size, angles between, degree of rounding, and/or specific shape of the patellar implant 100" and portions 102", 104", 106", 107", 108", 112", and 114" may also vary. In addition, the patellar implant 100" is used in a similar manner to and made from similar material(s) as the patellar implants 100/100'. The superior portion 102" has a convex upper surface and is still configured to lift and/or tilt the patellar tendon. The superior portion 102" is still to reside in proximity to the patellar tendon, while the inferior portion 104" is configured to be placed in proximity to the tibia. The inferior portion 104" has a concave portion 107" configured to fit the tibia of the patient. As a result, cutting, grinding, or other altering of the tibia in order to fit the implant 100" may be avoided. However, in another embodiment, the concave portion 107" may be omitted. Once in place, the patellar implant 100" may be affixed in place through a variety of mechanisms, described below. The patellar implant 100" might be affixed to the tibia, the patellar tendon, or both.

Through the use of the patellar implant 100", the patellar tendon may be lifted and/or tilted and the patella repositioned. In addition, the patellar implant 100" is wedged shaped. Thus, the lateral surface 110" is wider than the rounded edge 108". As a result, the patellar implant 100" tends to tilt the patellar tendon toward the rounded edge 108". Consequently, the ability of the patellar implant 100" to tilt the patellar tendon is improved. A greater tilt of the patellar tendon, as well as the patella, may thus be achieved. Consequently, pain and/or other issues related to patellar-femoral joint problems may be alleviated. Because cutting or other alteration of the tibia may be avoided if the concave portion 107" is provided, recovery time and ease of use of the patellar implant 100" may be improved.

Figure 4:
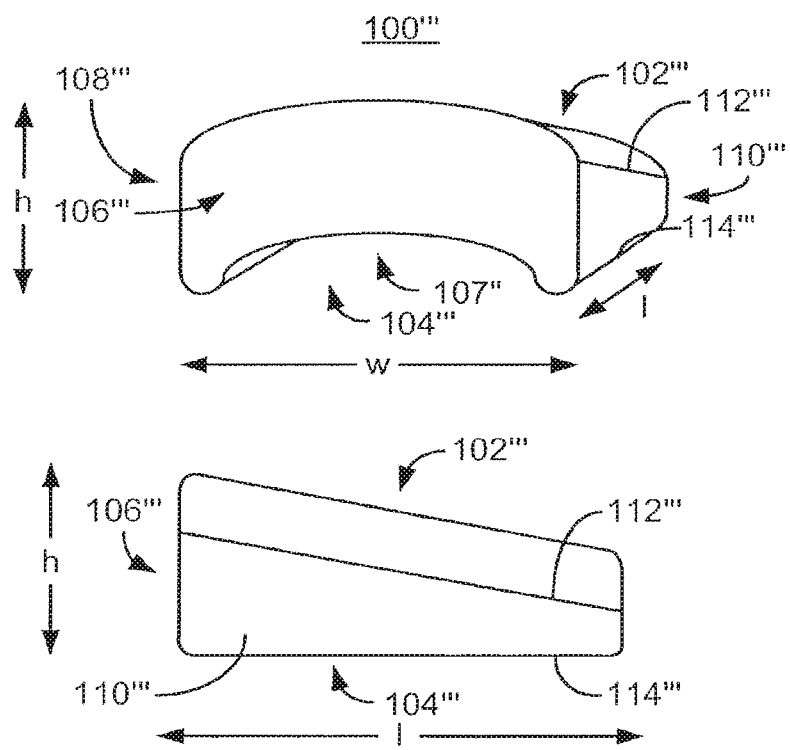
FIG. 4 depicts another exemplary embodiment of a patellar implant.

FIG. 4 depicts another exemplary embodiment of a patellar implant 100'''. For clarity, both perspective and side views are shown in FIG. 4. In addition, FIG. 4 is not drawn to scale. The components of the patellar implant 100''' are analogous to the patellar implants 100, 100', and 100". Thus, the components of the patellar implant 100''' are labeled similarly. The patellar implant 100''' includes a superior portion 102', an inferior portion 104''', anterior portion 106''', and posterior portion (not shown in FIG. 4). However, the patellar implant 100''' is tapered. In particular, lateral surfaces 108''' and 110''' are thicker near the anterior portion 106''. As for the patellar implants 100, 100', and 100", the amount of lift and/or tilt of the patellar tendon may vary between patients. Consequently, the size, angles between, degree of rounding, and/or specific shape of the patellar implant 100''' and portions 102''', 104''', 106''', 107''', 108''', 110'', 112''', and 114''' may also vary. In addition, the patellar implant 100''' is used in a similar manner to and made from similar material(s) as the patellar implants 100/100'/100".

The superior portion 102''' has a convex upper surface and is still configured to lift and/or tilt the patellar tendon. The superior portion 102''' is still to reside in proximity to the patellar tendon, while the inferior portion 104''' is configured to be placed in proximity to the tibia. The inferior portion 104''' has a convex portion 107''' configured to fit the tibia of the patient. As a result, cutting, grinding, or other altering of the tibia in order to fit the implant 100''' may be avoided. However, in another embodiment, the concave portion 107''' may be omitted. Once in place, the patellar implant 100''' may be affixed in place through a variety of mechanisms, described below. The patellar implant 100' might be affixed to the tibia, the patellar tendon, or both.

In addition, the patellar implant 100' is tapered. Thus, the superior portion 102''' is higher at the anterior portion 106' (nearer to the patella) than at the posterior portion (closer to the distal attachment of the patellar tendon). As a result, the elevation and/or tilt provided by the patellar implant 100''' may place less stress on the patellar tendon. Consequently, the comfort and/or usability of the patellar implant 100''' may be improved. Thus, the patellar implant 100''' may be used to tilt and/or lift the patellar tendon and reposition the patella. Consequently, pain and/or other issues related to patellar-femoral joint problems may be alleviated. Because cutting or other alteration of the tibia may be avoided if the concave portion 107''' is provided, recovery time and ease of use of the patellar implant 100''' may be improved. Further, because the patellar implant 100''' is tapered, the stress on the patellar tendon may be reduced.

Figure 5:
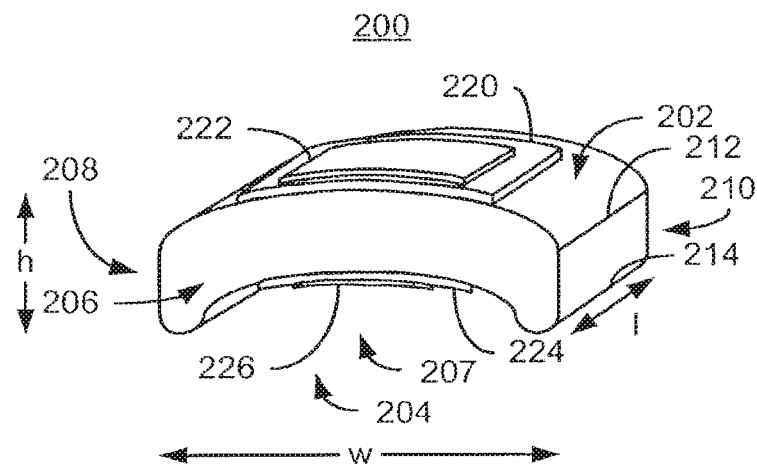
FIG. 5 depicts another exemplary embodiment of a patellar implant.

FIG. 5 depicts another exemplary embodiment of a patellar implant 200. For clarity, FIG. 5 is not drawn to scale. The components of the patellar implant 200 are analogous to the patellar implants 100/100'/100'''. Thus, the components of the patellar implant 200 are labeled similarly. The patellar implant 200 includes a superior portion 202, an inferior portion 204, anterior portion 206, and posterior portion (not shown in FIG. 5) corresponding to the superior portion 102/102'/102''/102''', inferior portion 104/104'/104''/104''', and anterior 106/106'/106''/106'''. As for the patellar implants 100, 100'. 100'' and or 100''', the amount of lift and/or tilt of the patellar tendon may vary between patients. Consequently, the size, angles between, degree of rounding, and/or specific shape of the patellar implant 200 and portions 202, 204, 206, 207, 208, 210, 212, and 214 may also vary. In addition, the patellar implant 200 is used in a similar manner to and made from similar material(s) as the patellar implants 100/100'/100''/100'''.

In addition, layers 220, 222, 224 and 226 are shown. In the embodiment shown, the layers 220 and 222 are configured to be added to the superior portion 204. The layers 224 and 226 are configured to be added to the inferior portion 202. By adding one or more of the layers 220 and 222, the height, h, of the patellar implant 100'' may be increased. In addition, note that the layers 220 and 222 do not extend across the width, w, of the patellar implant 200. As a result, the layers 220, 222, 224, and/or 226 may be used to adjust the tilt to the patellar tendon provided by the patellar implant 200. The layers 220 and 222 do not extend along the entire length of the patellar implant and/or may be tapered. The layers 220 and 222 may be used to alter the height of the patellar implant 200 along its length. Stated differently, the taper of the patellar implant 200 may be configured using the layers 220 and/or 222. In another embodiment, the amount each of the layers 220, 222, 224, and/or 226 extend along the height, width, and length of the patellar implant 200 as well as the location of the layers 220, 222, 224, and/or 226 on the patellar implant 200 may be selected. Although not shown, layers that may be added to the anterior portion 206 and/or the posterior portion (not shown) to increase the length of the patellar implant 200. Consequently, the patellar implant 200 may be configured by the surgeon or other qualified individual when being prepared for use in a patient.

The superior portion 202 has a convex upper surface, is symmetric, and is still configured to lift and/or tilt the patellar tendon. The superior portion 202 is still to reside in proximity to the patellar tendon, while the inferior portion 204 is configured to be placed in proximity to the tibia. The inferior portion 204 has a convex portion 207 configured to fit the tibia of the patient. As a result, cutting, grinding, or other altering of the tibia in order to fit the implant 100'' may be avoided. Once in place, the patellar implant 200 may be affixed in place through a variety of mechanisms, described below. The patellar implant 200 might be affixed to the tibia, the patellar tendon, or both. In addition, as described above, the height, tilt, and/or taper of the patellar implant 200 may be configured for the needs of a particular patient. The patellar tendon may be lifted and/or tilted and the patella repositioned in a desired fashion. Consequently, pain and/or other issues related to patellar-femoral joint problems may be alleviated. Because cutting or other alteration of the tibia may be avoided, recovery time and ease of use of the patellar implant 200 may be improved. Further, use of the layers 220, 222, 224, and 226 may be used to adjust the elevation and/or tilt provided as well as the fit of the patellar implant 200 to the tibia. Consequently, use of the patellar implant 200 may be improved.

Figure 6:
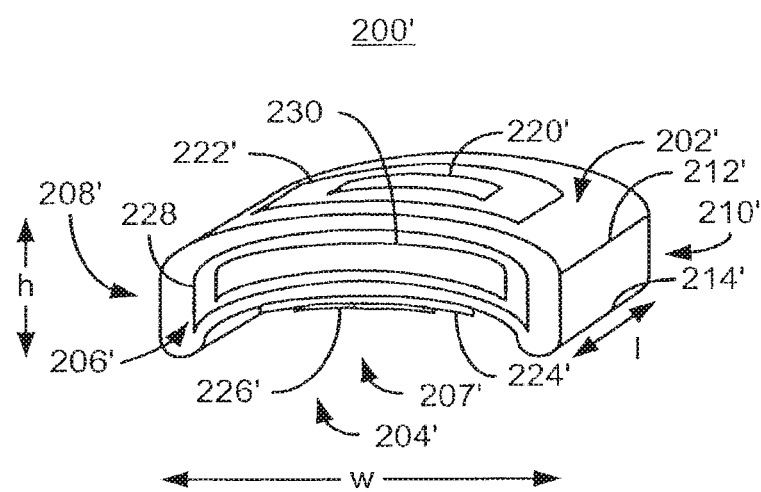
FIG. 6 depicts another exemplary embodiment of a patellar implant.

FIG. 6 depicts another exemplary embodiment of a patellar implant 200'. For clarity, FIG. 6 is not drawn to scale. The components of the patellar implant 200' are analogous to the patellar implants 200 and 100/100'/100'''. Thus, the components of the patellar implant 200' are labeled similarly. The patellar implant 200' includes a superior portion 202', an inferior portion 204', anterior portion 206', and posterior portion (not shown in FIG. 6). Also shown are lateral surfaces 108' and 110' as well as the edges 212' and 214'. As for the patellar implants 100/100'/100''/100''', the amount of lift and/or tilt of the patellar tendon may vary between patients. Consequently, the size, angles between, degree of rounding, and/or specific shape of the patellar implant 200' and portions 202', 204', 206', 207', 208', 210', 212', and 214' may also vary. In addition, the patellar implant 200' is used in a similar manner to the patellar implants 100/100'/100''/100''200.

In addition, nested sections 220', 222', 224', 226', 228, and 230 are shown. In the embodiment shown, the sections 220' and 222' are configured to be telescoped from the superior portion 204'. The sections 224' and 226' are configured to be, and shown as, telescoped from the inferior portion 202'. The sections 228 and 230 may be telescoped from the anterior portion 206. By telescoping the sections 220', 222', 224', 226', 228, and/or 230, the height and/or length of the patellar implant 100'' may be increased. In addition, the sections 220', 222', 224', and/or 226' might be used to adjust the tilt to the patellar tendon provided by the patellar implant 200'. The sections 220' and 222' do not extend along the entire length of the patellar implant and/or may be tapered. The sections 220' and 222' may be used to alter the height of the patellar implant 200' along its length. Stated differently, the taper of the patellar implant 200' may be configured using the sections 220' and/or 222'. The sections 224' and 226' may be used adjust the fit of the patellar implant 200' to the tibia. The sections 228 and 230 may be used to alter the length of the patellar implant 200'. In one embodiment, the amount each of the sections 220', 222', 224', 226', 228, and/or 230 extend along the height, width, and length of the patellar implant 200' may be selected. Consequently, the patellar implant 200' may be configured by the surgeon or other qualified individual when being prepared for use in a patient.

The superior portion 202' has a convex upper surface, is symmetric, and is still configured to lift and/or tilt the patellar tendon. The superior portion 202' is still to reside in proximity to the patellar tendon, while the inferior portion 204' is configured to be placed in proximity to the tibia. The inferior portion 204' has a convex portion 207' configured to fit the tibia of the patient. This fit may be improved using the sections 224' and 226'. As a result, cutting, grinding, or other altering of the tibia in order to fit the implant 200' may be avoided. Once in place, the patellar implant 200' may be affixed in place through a variety of mechanisms, described below. The patellar implant 200' might be affixed to the tibia, the patellar tendon, or both. In addition, as described above, the height, tilt, and/or taper of the patellar implant 200' may be configured for the needs of a particular patient. The patellar tendon may be lifted and/or tilted and the patella repositioned in a desired fashion. Consequently, pain and/or other issues related to patellar-femoral joint problems may be alleviated.

FIG. 7 depicts an exemplary embodiment of one option for placement of an exemplary embodiment of a patellar implant 100. For clarity, FIG. 7 is not drawn to scale. For simplicity, only the patellar implant 100 depicted in FIG. 1 is described. However, in other embodiments, other patellar implants including but not limited to the patellar implants 100', 100'', and 100''' may be used. Also shown in FIG. 5 are the tibia 150, femur 152, native-positioned patella 154, elevated-positioned patella 154', native-positioned patellar tendon 156, and elevated/tilted-positioned patellar tendon 156'. A patient may experience pain and other patellar-femoral joint problems when the patella tendon 156 and patella 154 are in their native positions. The patellar implant 100 is inserted between the patellar tendon 156 and the tibia 150, as well as between the patella 154 and the distal attachment 158 of the patellar tendon 156. The position of the patellar implant 100, as well as the shape and size of the patellar implant 100 may be selected in order to elevate and/or tilt the patellar tendon 156 in the desired manner. For example, for a smaller change in elevation, an implant having a lower height may be selected and/or a patellar implant 100 may be moved closer to the patella 154 and further from the distal attachment 158. In order to tilt the patellar tendon 156, a wedge shaped patellar implant, such as the implant 100''', may be selected and/or the patellar implant 100 may be placed at a different angle on the tibia 150 (e.g., further into or out of the plane of the page in FIG. 5). As a result, the patellar tendon 156' is moved to the elevated/tilted position. The change in position of the patellar tendon 156' causes a repositioning of the patella 154' to the elevated/tilted position. Thus, the patella 156' may be repositioned in order to alleviate pain or other patellar-femoral joint issues.

FIGS. 8-9 depict another exemplary embodiment of a patellar implant 300. For clarity, FIGS. 8-9 are not drawn to scale. The components of the patellar implant 300 are analogous to the patellar implants 100, 100', 100", 100''', 200, and 200'. Thus, the components of the patellar implant 300 are labeled similarly. However, for clarity, only a superior portion 302, an inferior portion 304, and anterior portion 306 are labeled. As for the patellar implants 100, 100', 100", 100''', 200, and 200' the amount of lift and/or tilt of the patellar tendon may vary between patients. Consequently, the size, angles between, degree of rounding, and/or specific shape of the patellar implant 300 and portions 302, 304, and 306 may also vary. In addition, the patellar implant is used in a similar manner to and made from similar material(s) as the patellar implants 200/200'/200".

The superior portion 302 has a convex upper surface and is still configured to lift and/or tilt the patellar tendon. The superior portion 302 is still to reside in proximity to the patellar tendon, while the inferior portion 304 is configured to be placed in proximity to the tibia. The inferior portion 304 has a convex portion (not separately labeled) configured to fit the tibia of the patient. As a result, cutting, grinding, or other altering of the tibia in order to fit the implant 300 may be avoided. However, in another embodiment, the concave portion may be omitted. Once in place, the patellar implant 100''' may be affixed in place through a variety of mechanisms, described below. The patellar implant 300 might be affixed to the tibia, the patellar tendon, or both.

Thus, the patellar implant 300 may be used to tilt and/or lift the patellar tendon and reposition the patella. Consequently, pain and/or other issues related to patellar-femoral joint problems may be alleviated. Because cutting or other alteration of the tibia may be avoided if the concave portion provided, recovery time and ease of use of the patellar implant 300 may be improved.

Figure 10:
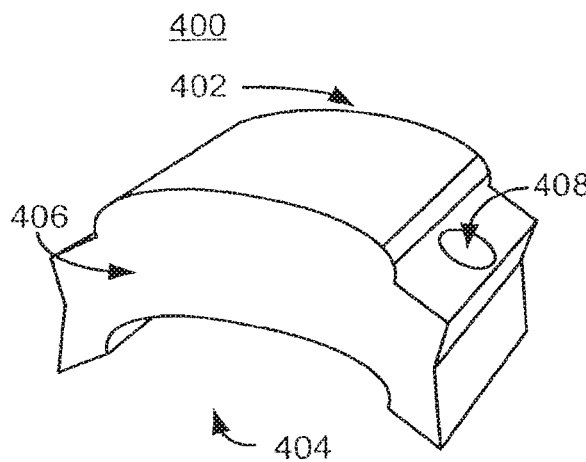
FIGS. 10 and 11 depict another exemplary embodiment of a patellar implant.
Figure 11:
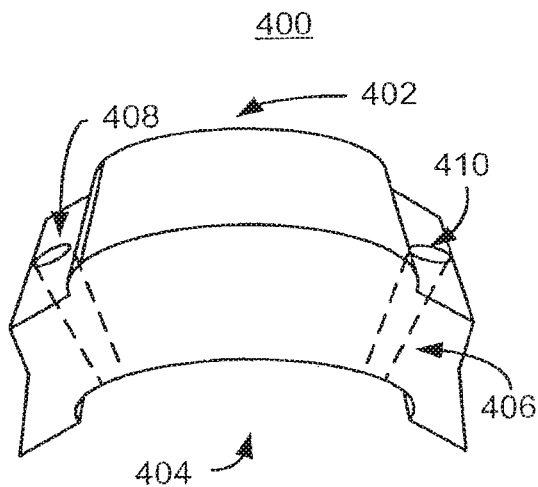

FIGS. 10-11 depict another exemplary embodiment of a patellar implant 400 that includes a mechanism for affixing the patellar implant. For clarity, FIGS. 10-11 are not drawn to scale. The components of the patellar implant 400 are analogous to the patellar implants 100, 100', 100", 100''', 200, 200', and 300. Thus, the components of the patellar implant 300 are labeled similarly. In addition, some components such as the through holes 408 and 410 are shown. However, for clarity, only a superior portion 402, an inferior portion 404, anterior portion 406, and through holes 408 and 410 are labeled. As for the patellar implants 100, 100', 100", 100''', 200, 200', and 300 the amount of lift and/or tilt of the patellar tendon may vary between patients. Consequently, the size, angles between, degree of rounding, and/or specific shape of the patellar implant 400 and portions 402, 404, 406, 408, and/or 410 may also vary. In addition, the patellar implant 400 is used in a similar manner to and made from similar material(s) as the patellar implants 100/100'/100"/100'''/200/200'/300.

The superior portion 402 has a convex upper surface and is still configured to lift and/or tilt the patellar tendon. The superior portion 402 is still to reside in proximity to the patellar tendon, while the inferior portion 404 is configured to be placed in proximity to the tibia. The inferior portion 404 has a convex portion (not separately labeled) configured to fit the tibia of the patient. As a result, cutting, grinding, or other altering of the tibia in order to fit the implant 400 may be avoided. However, in another embodiment, the concave portion may be omitted.

Once in place, the patellar implant 400 may be affixed in place through a variety of mechanisms. In the embodiment shown, through holes 408 and 410 may be used to affix the patellar implant 400. The through holes 408 and 410 extend through the top portion 402 and the inferior portion 404. In one embodiment, the holes 408 and 410 may be screw holes. In such an embodiment, the patellar implant 400 may be screwed to the tibia. In another embodiment, the through holes 408 and 410 might be suture holes used to suture the patellar implant to the patellar tendon. In yet another embodiment, a mixture of screw holes and suture holes might be used. Thus, the through holes 408 and 410 permit the patellar implant 400 to be mounted to various tissue adjacent to the implant's location.

Thus, the patellar implant 400 may be used to tilt and/or lift the patellar tendon and reposition the patella. Consequently, pain and/or other issues related to patellar-femoral joint problems may be alleviated.

Figure 12:
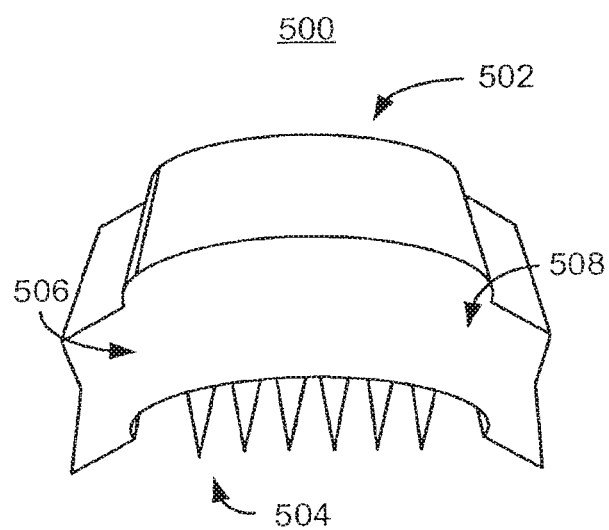
FIG. 12 depicts another exemplary embodiment of a patellar implant.

FIG. 12 depicts another exemplary embodiment of a patellar implant 500 that includes a mechanism for affixing the patellar implant. For clarity, FIG. 12 is not drawn to scale. The components of the patellar implant 500 are analogous to the patellar implants 100, 100', 100", 100''', 200, 200', 300, and 400. Thus, the components of the patellar implant 500 are labeled similarly. However, for clarity, only a superior portion 502, an inferior portion 504, anterior portion 506, and affixation spikes 508 are labeled. As for the patellar implants 100, 100', 100", 100''', 200, 200', 300, and 400 the amount of lift and/or tilt of the patellar tendon may vary between patients. Consequently, the size, angles between, degree of rounding, and/or specific shape of the patellar implant 500 and portions 502, 504, 506, and/or 508 may also vary. In addition, the patellar implant 500 is used in a similar manner to and made from similar material(s) as the patellar implants 100/100'/100"/100'''/200/200'/300/400.

The superior portion 502 has a convex upper surface and is still configured to lift and/or tilt the patellar tendon. The superior portion 502 is still to reside in proximity to the patellar tendon, while the inferior portion 504 is configured to be placed in proximity to the tibia. The inferior portion 504 has a convex portion (not separately labeled) configured to fit the tibia of the patient. As a result, cutting, grinding, or other altering of the tibia in order to fit the implant 500 may be avoided. However, in another embodiment, the concave portion may be omitted.

Once in place, the patellar implant 500 may be affixed in place through a variety of mechanisms. In the embodiment shown, affixation spikes 508 may be used to affix the patellar implant 500. The affixation spikes 508 may be mounted the patellar implant 500 to adjacent tissue, such as bone. Thus, the patellar implant 500 may be used to tilt and/or lift the patellar tendon and reposition the patella. Consequently, pain and/or other issues related to patellar-femoral joint problems may be alleviated.

FIG. 13 depicts another exemplary embodiment of a patellar implant 600 that includes a mechanism for affixing the patellar implant. For clarity, FIG. 13 is not drawn to scale. The components of the patellar implant 600 are analogous to the patellar implants 100, 100', 100", 100''', 200, 200', 300, 400, and 500. Thus, the components of the patellar implant 600 are labeled similarly. However, for clarity, only a superior portion 602, an inferior portion 604, anterior portion 606, and bone growth enhancement device 608 are labeled. As for the patellar implants 100, 100', 100", 100''', 200, 200', 300, 400, and 500 the amount of lift and/or tilt of the patellar tendon may vary between patients. Consequently, the size, angles between, degree of rounding, and/or specific shape of the patellar implant 600 and portions 602, 604, 606, and/or 608 may also vary. In addition, the patellar implant 500 is used in a similar manner to and made from similar material(s) as the patellar implants 100/100'/100"/100'''/200/200'/300/400/500.

The superior portion 602 has a convex upper surface and is still configured to lift and/or tilt the patellar tendon. The superior portion 602 is still to reside in proximity to the patellar tendon, while the inferior portion 604 is configured to be placed in proximity to the tibia. The inferior portion 604 has a convex portion (not separately labeled) configured to fit the tibia of the patient. As a result, cutting, grinding, or other altering of the tibia in order to fit the implant 600 may be avoided. However, in another embodiment, the concave portion may be omitted.

Once in place, the patellar implant 600 may be affixed in place through a variety of mechanisms. In the embodiment shown, the bone growth enhancement device 608 includes affixation beads 608. The affixation beads 608 are used to promote growth of bone, such as the tibia, with the patellar implant 608. Thus, the patellar implant 600 may be affixed in place and used to tilt and/or lift the patellar tendon and reposition the patella. Consequently, pain and/or other issues related to patellar-femoral joint problems may be alleviated.

Figure 16:
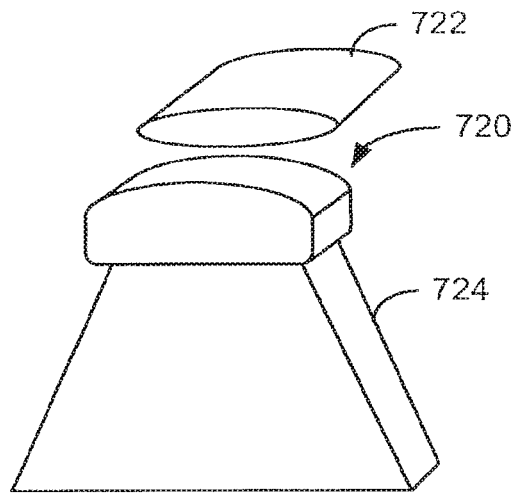
Figure 17:
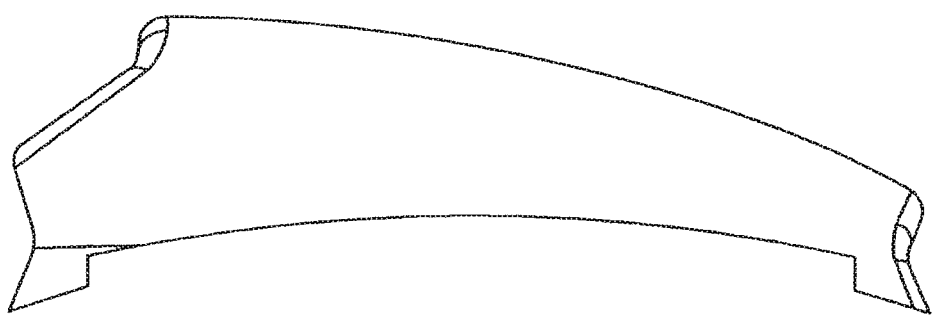
Figure 18:
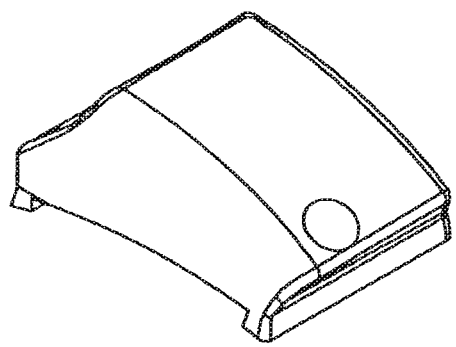
FIGS. 18, 19, 20, 21 and 22 depict another exemplary embodiment of a patellar implant.
Figure 19:
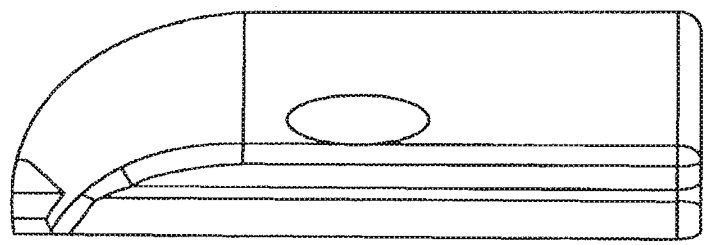
Figure 20:
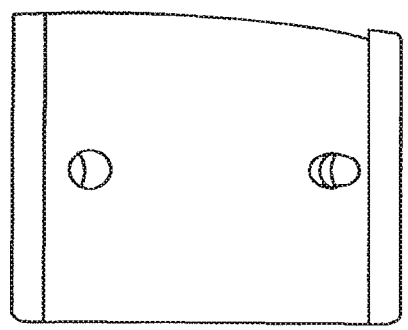
Figure 21:
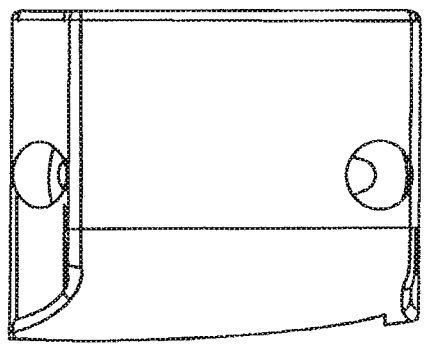
Figure 22:
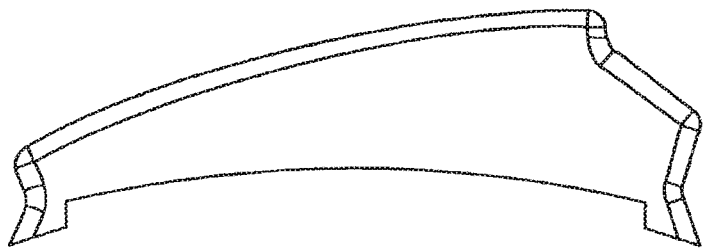

FIG. 14-16 depicts other exemplary embodiments of patellar implants 700, 710, and 720 positioned beneath a patellar tendon 702, 712, and 722, respectively, and on a tibia 704, 714, and 724, respectively. For clarity, FIGS. 14-16 are not drawn to scale. Thus, patellar implants which have a convex inferior surface 700, which are wedge shaped 710, or which are have a flat inferior surface 720 are shown. Thus, the patellar tendon 702 may be elevated, the patellar tendon 712 may be elevated and tilted, and the tibia 724 may be processed to provide a flat upper surface for affixing the patellar implant 722. The patellar implants 700, 710, and 720 may be affixed in place and used to tilt and/or lift the patellar tendon 702, 712, 714 and reposition the patella. Consequently, pain and/or other issues related to patellar-femoral joint problems may be alleviated.

FIGS. 17-22 depict another exemplary embodiment of a patellar implant 750. Front, perspective, side, bottom, top, and rear views are shown in FIGS. 17-22, respectively. For clarity, FIGS. 17-22 are not drawn to scale. The patellar implant 750 is substantially wedge shaped, has a concave inferior portion, a substantially convex superior portion, and through holes. Consequently, the benefits of the patellar implants discussed herein may be achieved.

Figure 23:
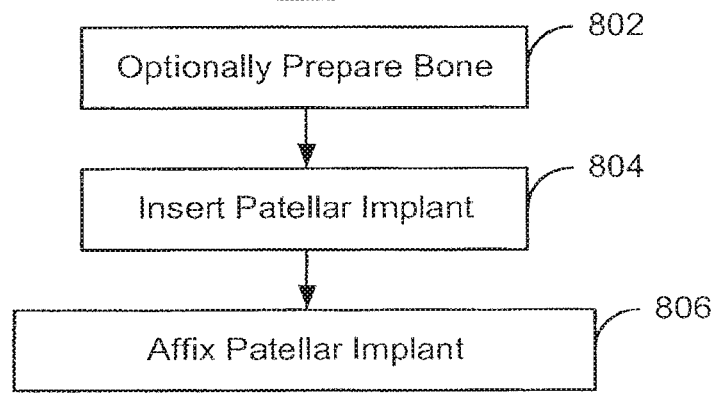
FIG. 23 depicts an exemplary embodiment of a method for placing a patellar implant.

FIG. 23 depicts an exemplary embodiment of a method 800 for placing a patellar implant, such as a patellar implant described herein. For simplicity, the method 800 is described in the context of the patellar implant 100. The bone is optionally prepared for the implant, via step 802. For example, step 802 might include cutting a slot or flat portion in the tibia, for example to be flat as is shown in FIG. 16. However, in other embodiments, preparing the bone may be performed in another manner or may be omitted. The patellar implant 100 is inserted between the patellar tendon and the tibia, as well as between the patella and the distal attachment of the patellar tendon to the tibia, via step 804. Step 804 may include providing a surgical incision, for example 2-3 cm in length. In one embodiment, step 804 is performed using minimally invasive techniques. Further, the prepatellar fat pad may be removed. As part of step 804, arthroscopic evaluation may be performed to assess tracking and assist with intraoperative decision making.

Step 804 may also include determining the desired tilt and/or elevation for the patellar implant 100. Although an assessment may have been made prior to surgery, the final decisions on elevation and tilt, as well as size, shape, placement and other relevant characteristics of the patellar implant 100 may be made during surgery. Step 802, therefore, may also include selecting and/or adjusting the patellar implant as well as determining the final placement of the implant 100. For example, the patellar implant 100 at or near a desired size and shape may be selected in step 804 In addition, if layers are to be added, sections telescoped or other adjustments made, these adjustments are preferably completed in step 802, prior to the patellar implant 100 being affixed within the patient. In another embodiment, the configuration of the patellar implant 100 may still be adjusted at a later time.

Once appropriate elevation and/or tilt of the patella implant 100, and thus the patellar tendon and patella, have been achieved, the patellar implant 100 may be affixed, via step 804. In one embodiment, the patellar implant 100 is fixated to the proximal tibia, to the patellar tendon, or both. Fixation may be accomplished by using any fixation device, including but not limited to those described herein. For example, fixation may be achieved using a screw, sutures, nail(s), bone cement or other adhesives, or direct attachment to the patella tendon.

Using the method 800, a patellar implant, such as the implants 100, 100', 100", 100''', 200, 200', 400, 500, and/or 600 may be placed in a patient. Consequently, the therapeutic benefits of the implant may be achieved.

A method and system for a patellar implant has been disclosed. The method and system have been described in accordance with the embodiments shown, and one of ordinary skill in the art will readily recognize that there could be variations to the embodiments, and any variations would be within the spirit and scope of the present application. Accordingly, many modifications may be made by one of ordinary skill in the art without departing from the spirit and scope of the appended claims.

What is claimed is:

1. An implant sized and configured to be inserted through an incision during a surgical procedure and affixed to a tibia at an implant location beneath the patellar tendon such that the entire implant is between an end of the tibia proximate a femur and an attachment position of the patellar tendon to the tibia, the implant comprising:

a first portion configured to be in proximity to a patella when the implant is at the implant location;
a second portion opposite to the first portion;
a third portion having a length extending between the first portion and the second portion and a width extending between a fifth portion and a sixth portion, the third portion comprising a curved surface configured to extend over the tibia when the implant is at the implant location;
a fourth portion opposite to the third portion and configured to change a position of the patellar tendon by elevating or lifting the patellar tendon when the implant is at the implant location;
the fifth portion having a length extending between the first portion and the second portion and a height extending between the third portion and the fourth portion; and
the sixth portion being opposite to the fifth portion, the sixth portion having a length extending between the first portion and the second portion and a height extending between the third portion and the fourth portion, the height of the sixth portion being greater than the height of the fifth portion such that the implant has a wedge-shaped cross-section.

2. The implant of claim 1 wherein the curved surface of the third portion extends between first and second rounded edges.

3. The implant of claim 2 wherein the first and second rounded edges extend from the first portion to the second portion.

4. The implant of claim 1 wherein the fourth portion comprises a convex surface.

5. The implant of claim 1 wherein the sixth portion comprises a flat surface.

6. The implant of claim 1 further comprising an affixation mechanism.

7. An implant sized and configured to be inserted through an incision during a surgical procedure and affixed to a tibia at an implant location beneath the patellar tendon such that the entire implant is between an end of the tibia proximate a femur and an attachment position of the patellar tendon to the tibia, the implant comprising:
a first portion configured to be in proximity to a patella when the implant is at the implant location;
a second portion opposite to the first portion;
a third portion having a length extending between the first portion and the second portion and a width extending between a fifth portion and a sixth portion, the third portion comprising a curved surface extending between first and second rounded edges and configured to extend over the tibia when the implant is at the implant location;
a fourth portion opposite to the third portion and configured to change a position of the patellar tendon by elevating or lifting the patellar tendon when the implant is at the implant location;
the fifth portion disposed adjacent the first rounded edge and having a length extending between the first portion and the second portion and a height extending between the third portion and the fourth portion; and
the sixth portion being opposite to the fifth portion, the sixth portion being disposed adjacent the second rounded edge and having a length extending between the first portion and the second portion and a height extending between the third portion and the fourth portion, the height of the sixth portion being greater than the height of the fifth portion such that the implant has a wedge-shaped cross-section.

8. The implant of claim 7 wherein the first and second rounded edges extend from the first portion to the second portion.

9. The implant of claim 7 wherein the fourth portion comprises a convex surface.

10. The implant of claim 7 wherein the sixth portion comprises a flat surface.

11. The implant of claim 7 further comprising an affixation mechanism.

12. An implant sized and configured to be inserted through an incision during a surgical procedure and affixed to a tibia at an implant location beneath the patellar tendon such that the entire implant is between an end of the tibia proximate a femur and an attachment position of the patellar tendon to the tibia, the implant comprising:
a first portion configured to be in proximity to a patella when the implant is at the implant location;
a second portion opposite to the first portion;
a third portion having a length extending between the first portion and the second portion and a width extending between a fifth portion and a sixth portion, the third portion comprising a curved surface configured to extend over the tibia when the implant is at the implant location;
a fourth portion opposite to the third portion and configured to change a position of the patellar tendon by elevating or lifting the patellar tendon when the implant is at the implant location, a maximum distance between the third portion and the fourth portion defining an implant height between 0.5 cm and 3 cm;
the fifth portion having a length extending between the first portion and the second portion and a height extending between the third portion and the fourth portion; and
the sixth portion being opposite to the fifth portion, the sixth portion having a length extending between the first portion and the second portion and a height extending between the third portion and the fourth portion, the height of the sixth portion being greater than the height of the fifth portion such that the implant has a wedge-shaped cross-section.

13. The implant of claim 12 wherein a distance between the fifth portion and the sixth portion defines a width of the implant between 1 cm and 3.5 cm.

14. The implant of claim 12 wherein the curved surface of the third portion extends between first and second rounded edges.

15. The implant of claim 14 wherein the first and second rounded edges extend from the first portion to the second portion.

16. The implant of claim 12 wherein the fourth portion comprises a convex surface.

17. The implant of claim 12 wherein the sixth portion comprises a flat surface.

18. The implant of claim 12 further comprising an affixation mechanism.

* * * * *